United States Patent [19]

Konishi et al.

[11] 3,998,550
[45] Dec. 21, 1976

[54] PHOTOELECTRIC OXIMETER

[75] Inventors: Masaichiro Konishi, Suita; Tohru Kisanuki, Toyokawa; Akio Yamanishi, Tondabayashi; Yutaka Majima, Toyokawa, all of Japan

[73] Assignee: Minolta Camera Corporation, Osaka, Japan

[22] Filed: Oct. 10, 1975

[21] Appl. No.: 621,278

[30] Foreign Application Priority Data

Oct. 14, 1974 Japan .............................. 49-118543

[52] U.S. Cl. .............................. 356/39; 128/2 L; 356/41; 356/181
[51] Int. Cl.[2] .......................................... G01N 33/16
[58] Field of Search ............... 356/39, 40, 41, 178, 356/181; 128/2 L

[56] References Cited

UNITED STATES PATENTS

| 2,640,389 | 6/1953 | Liston | 356/41 |
|---|---|---|---|
| 3,628,525 | 12/1971 | Polanyi et al. | 356/41 |
| 3,704,706 | 12/1972 | Herczfeld et al. | 356/41 |

OTHER PUBLICATIONS

"Photoelectric Determination of Arterial Oxygen Saturation in Man," Wood et al; Journal of Laboratory & Clinical Medicine; vol. 34, 1949; pp. 387–401.

*Primary Examiner*—Vincent P. McGraw
*Attorney, Agent, or Firm*—Jackson & Jones Law Corporation

[57] ABSTRACT

An optical non-invasive oximeter for measuring oxygen saturation in arterial blood utilizes a light source capable of giving off light having different wavelengths, such as light in the infrared and red region, and a pair of photoelectric devices, one responding to one wavelength and the other to the other wavelength, for detecting the amount of such light transmitted through living tissue. Each photoelectric device is connected to a computing circuit which generates a signal that represents the logarithm of the quotient of the signal received from the photoelectric device divided by its direct current component. The signals from each of the computing circuits are differentiated and then divided, one by the other, to provide an indication of oxygen saturation in the blood.

19 Claims, 11 Drawing Figures

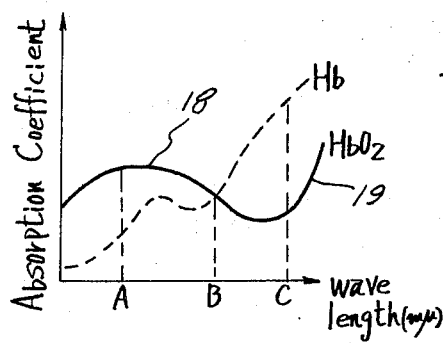
Fig. 3
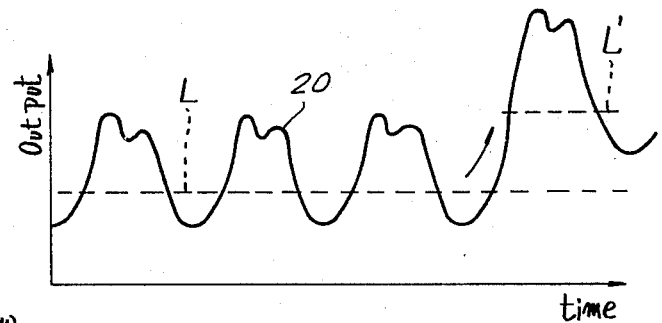
Fig. 4
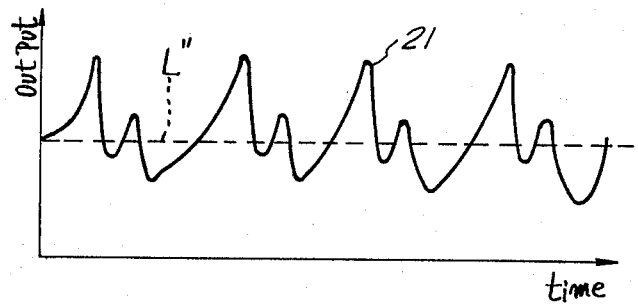
Fig. 5
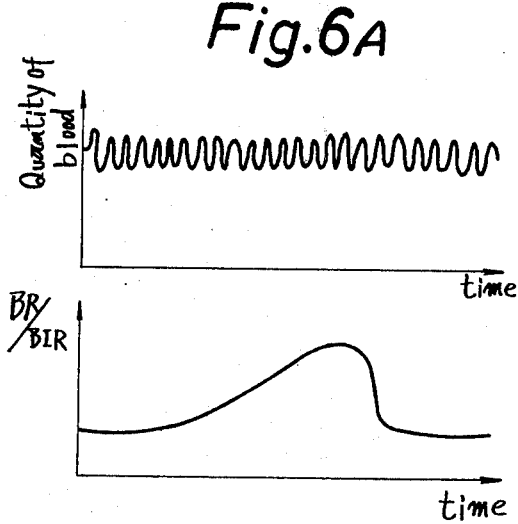
Fig. 6A
Fig. 6B

3,998,550

PHOTOELECTRIC OXIMETER

BACKGROUND OF THE INVENTION

1. Field of the Invention

The present invention relates generally to a non-invasive oximeter capable of measuring arterial oxygen saturation, and more particularly, to an optical oximeter which analyzes light wave signals transmitted through a living body to detect the oxygen saturation in the arterial blood contained therein.

2. Description of the Prior Art

In general, methods for measuring oxygen saturation in arterial blood without penetrating body tissue utilize the relative difference between the light absorption coefficient of hemoglobin (Hb) and that of the hemoglobin oxide (HbO$_2$). The light absorption coefficient for Hb and HbO$_2$ is characteristically tied to the wavelength of the light traveling through them. Both Hb and HbO$_2$ transmit light having a wavelength in the infrared region to approximately the same degree. However, in the visible region, the light absorption coefficient for Hb is quite different from the light absorption coefficient of HbO$_2$.

One example of a non-invasive oximeter is described in an article titled "Photoelectric Determination of Arterial Oxygen Saturation in Man" by Wood and Geraci, in the Journal of Laboratory and Clinical Medicine, Volume 34, 1949. The oximeter described therein utilizes a light source that generates light in the infrared region and in the red region. Both light wave signals are transmitted through body tissue. The respective light wave signals leaving the body tissue are photoelectrically converted into a first and second output signal. Ultimately, these signals are analyzed to get an indication of the oxygen saturation in the arterial blood. Before these first and second signals are generated, the body tissue is compressed to occlusive pressure (200 mm. of mercury), squeezing blood from the tissue under test. This is done to obtain reference output signals which have information regarding light absorption by the tissue itself, i.e., muscles, bone or skin, without the blood. These reference signals are required in order to separate the information regarding light absorption by blood alone from the above mentioned first and second output signals, which includes information regarding light absorption by the blood and tissue together.

As a result of this tissue compression set up, it is impossible to continuously detect the oxygen saturation in the blood, because a measurement under compression interrupts the normal flow of blood. As a result of the necessity of providing a compression pressure of 200 mm. of mercury, this prior art oximeter is quite bulky and cumbersome, and may even introduce a certain amount of discomfort to the subject.

SUMMARY AND OBJECTS OF THE INVENTION

An object of the present invention is to provide means in an oximeter for obtaining information regarding light absorption by blood alone without compressing the tissue under test.

Another object of the present invention is to provide an oximeter which does not compress the tissue under test.

Still another object of the present invention is to provide an oximeter circuit in which the fluctuations of the reference level of the pulsating output signal is removed to increase the reliability of the measurement.

The above objects as well as the general purpose of the present invention, is accomplished by utilizing a pair of computing circuits, each computing circuit receiving signals from its respective photoelectric device. Each computing circuit includes a circuit for separating the direct current component from the received photoelectrically converted signal. A circuit combination in the computing circuit takes the received photoelectrically converted signal and the separated out direct current component and provides an output signal representative of the logarithm of the quotient of the received photoelectric signal divided by the direct current component. The respective signals from the computing circuits are differentiated and then divided, one by the other, to provide an indication of oxygen saturation in the blood.

BRIEF DESCRIPTION OF THE DRAWINGS

Other objects and many of the attendant advantages of this invention will be readily appreciated as the same becomes better understood by reference to the following detailed description when considered in conjunction with the accompanying drawings in which like reference numerals designated like parts throughout the figures thereof and wherein:

FIG. 3 is a graph representing variation in the light absorption coefficient of hemoglobin and hemoglobin oxide versus the wavelength of light.

FIG. 4 is a graph illustrating the final output signal from the circuit of FIG. 1.

FIG. 5 is a graph representing the output signals from each of the differentiation circuits of FIG. 2.

FIG. 6A is a graph showing the variation in the quantity of blood in an artery, in terms of time.

FIG. 6B is a graph showing the variation in the ratio between light absorption coefficients of the blood at first and second wavelengths in terms of time.

DESCRIPTION OF THE PREFERRED EMBODIMENT

Figure 1:
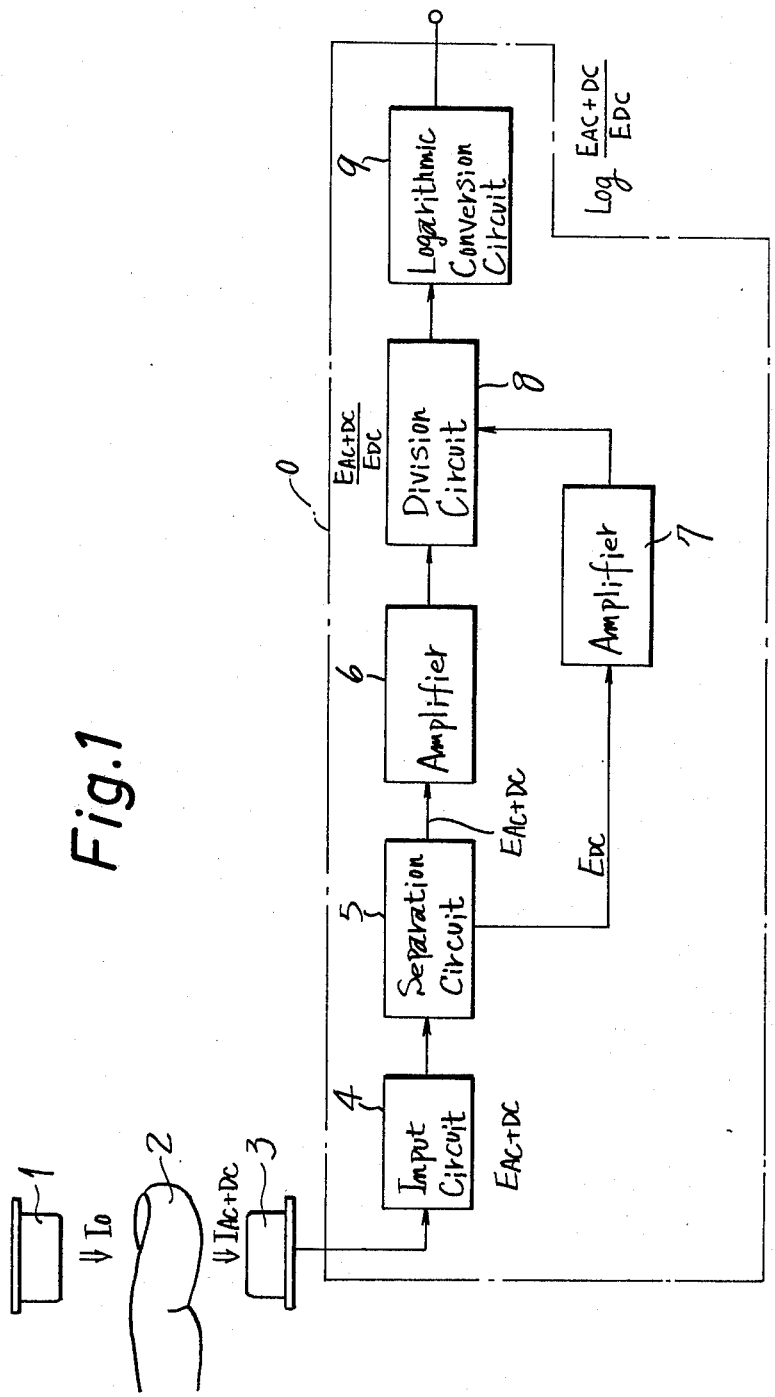
FIG. 1 is a block diagram of a preferred embodiment of a portion of the present invention.

Referring to FIG. 1, a light source 1, such as a light emitting diode or the like, emits a quantity of light $I_o$. A great majority of the quantity of light $I_o$ being emitted is passed to a living body 2, such as a finger tip, where a portion thereof is absorbed. The portion not absorbed becomes a final quantity of light $I_{AC+DC}$ which contains an AC component relating to absorption by the pulsating blood in the arteries, and a DC component relating to absorption by the tissue in the body 2, $I_{AC+DC}$ can be represented by the following equation:

$$I_{AC+DC} = I_o F_T e^{-R(d+l)} \qquad 1.$$

wherein:

$\beta$ is the absorption coefficient of blood $F_T$ is a light-quantity attenuation index for the absorption of light by the body tissue;

$d$ is a quantity of blood that remains in the tissue on a steady-state basis; and $l$ is the quantity of blood which varies in terms of time due to pulsation.

A photoelectric device 3, including a CDS, CDSe, or silicon photodiode, produces an output signal:

$$E = A I^\gamma$$

for a quantity I of light incident thereupon. The output ($E_{AC+DC}$) quantity of light $I_{AC+DC}$ is represented by the expression:

$$E_{AC+DC} = A I^\gamma_{AC+DC}$$

substituting for $I_{AC+DC}$ from equation 1:

$$E_{AC+DC} = A [I_o \ F_T \ e^{-\beta (d+l)}]^\gamma$$
$$= A \ I_o^\gamma \ F_T^\gamma \ e^{-\beta\gamma d} \ e^{-\beta\gamma l} \quad \quad 2$$

wherein A and $\gamma$ are constants.

A separation circuit 5 receives the $E_{AC+DC}$ from the input circuit 4 and provides the DC component $E_{DC}$ to one output terminal and the received signal $E_{AC+DC}$ to the other output terminal. From equation (2), it can be seen that only the variable $l$ is changed in terms of time, and $E_{DC}$ can be expressed as follows:

$$E_{DC} = A \ I_o^\gamma F_T^\gamma e^{-\beta\gamma d} \quad \quad 3.$$

Amplifiers 6 and 7 amplify the signals $e_{AC+DC}$ and $E_{DC}$ respectively received from the separation circuit 5. The outputs of both amplifiers are connected to a division circuit 8, in which a division $E_{AC+DC}/E_{DC}$ is effected. From equations 2 and 3, the output signal from the dividing circuit 8 can be represented by the following expression:

$$E_{AC+DC}/E_{DC} = e^{-\beta\gamma l} \quad \quad 4.$$

A logarithmic conversion circuit 9 receives this signal from the division circuit 8. From equation (4), the output signal Y from the logarithmic conversion circuit 9 can be expressed as follows:

$$Y = \log (E_{AC+DC}/E_{DC}) = -\beta\gamma l \log e \quad \quad 5.$$

From equation (5), since $\gamma \log e$ is a constant having a predetermined value, the output signal Y supplies information about $\beta l$, the absorption coefficient of blood times a certain quantity of blood. As a result, the embodiment of FIG. 1 will supply a signal that indicates the degree of absorption of the light generated by the light source 1, by the blood in the arteries. As can be seen from FIG. 1, this is accomplished without compression of the body tissue 2, and without impeding the flow of blood in any way.

Since $\log (E_{AC+DC}/E_{DC})$ is desired, a more convenient equivalent for the embodiment of FIG. 1 may comprise a circuit, which is arranged so that $E_{AC+DC}$ and $E_{DC}$ is converted into logarithmic form first and the division circuit substituted by a subtraction circuit for subtracting $\log E_{DC}$ from $\log E_{AC+DC}$. The end result is the same.

Figure 2:
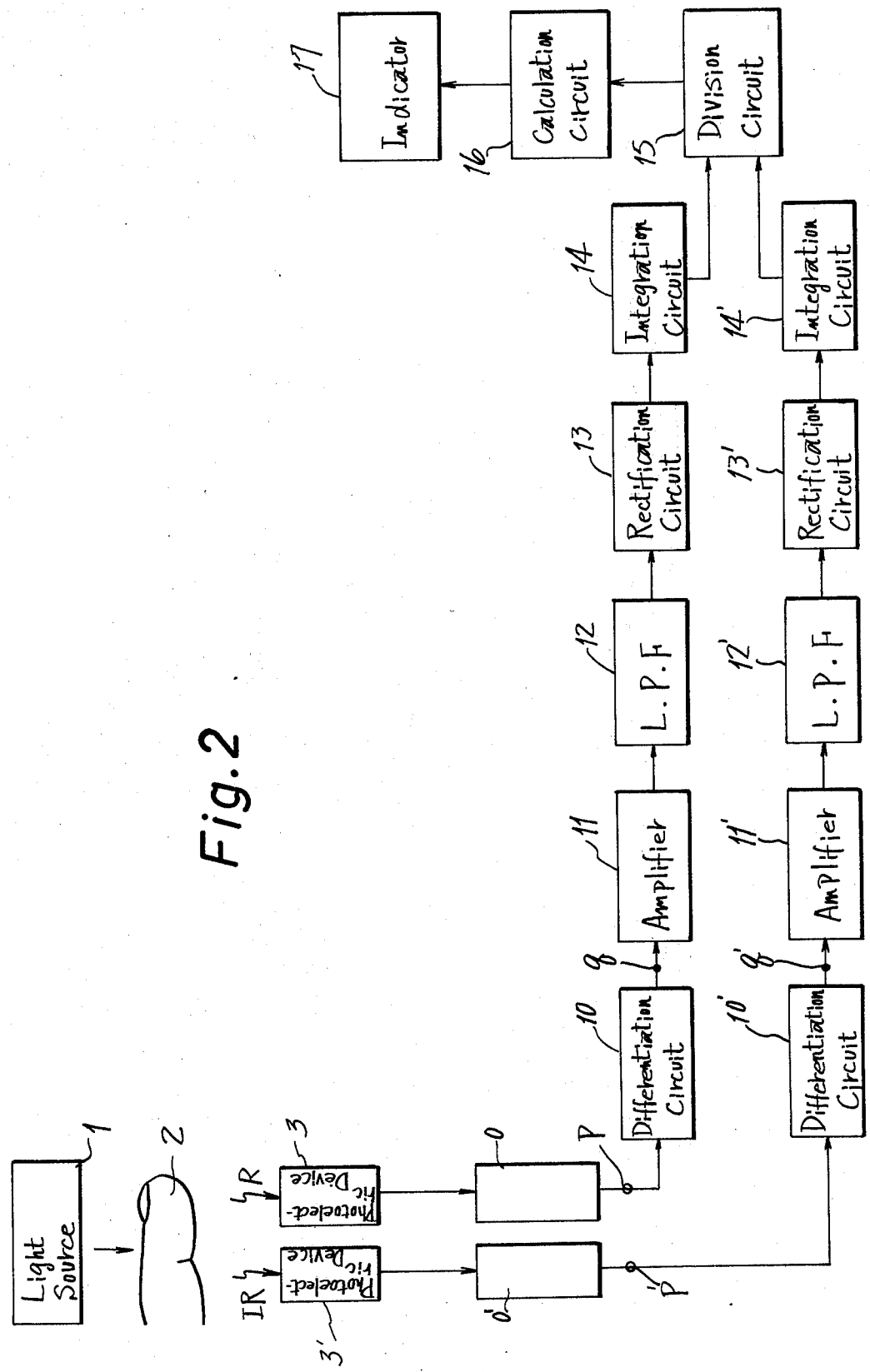
FIG. 2 is a block diagram of a preferred embodiment of an oximeter according to the present invention.

FIG. 2 illustrates a preferred embodiment of an oximeter which utilizes a pair of signal generating circuits 0,0' of the type shown in FIG. 1. A first photoelectric device 3, connected to a first computing section 0 is arranged to receive light having first wavelength (R) that may be in the red region. A second photoelectric device 3', which may be identical to the first photoelectric device 3, except for its light filter, is connected to a second computing section 0'. This photoelectric device is arranged to receive light having a second wavelength (IR) that may be in the infrared region.

Referring to FIG. 3, the characteristic change in the light absorption coefficient of hemoglobin (Hb) and that of hemoglobin oxide ($HbO_2$), in relation to the wavelength of light is plotted. As can be seen from the graph, the absorption coefficient 18 of hemoglobin is equal to the absorption coefficient 19 of hemoglobin oxide for light having a wavelength B, in the infrared region. When light having a wavelength A, in the red region, or C, above infrared, is used, the absorption coefficients for Hb and $HbO_2$ differ considerably.

Referring again to FIG. 2, the photoelectric devices in the Y signal generating circuits 0 and 0' are structured to receive light at different wavelengths, for example, by the selection of appropriate filters for the photoelectric devices 3 and 3'. As a result, the output signal from signal generating circuit 0 will be different from the output signal from signal generating circuit 0'. Equation (5) expresses the output Y for each of the signal generating circuits as follows:

$$Y_R = +\beta_R \gamma l \log e \quad \quad 6.$$

$$Y_{IR} = -\beta_{IR} \gamma l \log e \quad \quad 7.$$

where:

$Y_R$ and $Y_{IR}$ are representative of the outputs from the respective circuits 0 and 0' $\beta_R$ and $\beta_{IR}$ are the light absorption coefficient of the blood in terms of light having a first wavelength (R) and light having a second wavelength (IR), respectively The absorption coefficients $\beta_R$ and $\beta_{IR}$ can be expressed as follows:

$$\beta_R = A_R(HbO_2)C(HbO_2) + A_R(Hb)C(Hb) \quad \quad 8.$$

$$\beta_{IR} = A_{IR}(HbO_2)C(HbO_2) + A_{IR}(Hb)C(Hb) \quad \quad 9.$$

wherein:

$A_R(HbO_2)$ represents the light absorption coefficient of $HbO_2$ in terms of light having a first wavelength, $A_R(Hb)$ represents the light absorption coefficient of Hb in terms of light having a first wavelength, $A_{IR}(HbO_2)$ represents the light absorption coefficient of $HbO_2$ in terms of light having a second wavelength, $A_{IR}(Hb)$ represents the light absorption coefficient of Hb in terms of light having a second wavelength $C(HbO_2)$ is representative of the density of $HbO_2$ in the blood, $C(Hb)$ is representative of the density of Hb in the blood.

The quantity to be measured is oxygen saturation (S) of the blood. S is defined according to the variables of equations (8) and (9), as follows:

$$S = C(HbO_2)/(C(HbO_2) + C(Hb)) \quad \quad 10.$$

From equations (8) and (9), equation (10) may be transformed in terms of absorption coefficient as follows:

$$S = \frac{A_{IR}(Hb)\beta_R/\beta_{IR} - A_R(Hb)}{(A_{IR}(Hb) - A_{IR}(HbO_2))\beta_R/\beta_{IR} + A_R(HbO_2) - A_R(Hb)} \quad (11)$$

All the terms of equation (11), other than $\beta_R/\beta_{IR}$ are constants which can be determined beforehand. As a result S (oxygen saturation) can be calculated when the ratio $\beta_R/\beta_{IR}$ is known. If a lightwave having a length B in the infrared region is selected as the IR signal, then $A_{IR}(Hb) = A_{IR}(HbO_2)$, see FIG. 3, and therefore, the equation (11) is represented in the form:

$$S = \frac{A_{IR}(HbO_2)}{A_R(HbO_2) - A_R(Hb)} \beta_R/\beta_{IR} - \frac{A_R(Hb)}{A_R(HbO_2) - A_R(Hb)} \quad (12)$$

By connecting a dividing circuit, such as division circuit 15, to the output terminals P and P' of the Y signal generating circuits 0 and 0', respectively, $Y_R Y_{IR}$ is obtained. According to equations (6) and (7), the following relationship exists:

$$Y_R/Y_{IR} = \beta_R/\beta_{IR} \quad 13.$$

Either equation (11) or (12) will supply a measure of oxygen saturation (S), $\beta_R/\beta_{IR}$ being the only variable therein.

The signal $Y_R/Y_{IR}$ obtained from the divider circuit connected to the output of the two Y signal generating circuits 0 and 0' is not in an optimized condition. Due to instability, which is largely dependent on respiration of the patient, the output signal fluctuates widely. Due to the time constant of a smoothing circuit included in the separation circuit 5 (FIG. 1), a reference level of the Y output signal from the Y signal generating circuits fluctuates as represented by curve 20 in FIG. 4. The reference level is shown as fluctuating between a level L and L'. This fluctuation affects the computation of the output signal Y, possibly leading to error in the final indication.

To eliminate this possibility, the output signals $Y_R$ and $Y_{IR}$, from their respective circuits are fed as inputs to differentiation circuits 10 and 10', respectively, shown in FIG. 2. The representative output signal 21 from the differentiation circuits 10 and 10' has a reference level L'', as shown in FIG. 5. This reference level is constant, and not under the influence of the fluctuation in the reference level of the output signals $Y_R$ and $Y_{IR}$, respectively. From equations (6) and (7) the output signals from the differentiation circuits 10 and 10' can be represented as follows:

$$\frac{dY_R}{dt} = -\gamma \beta_R \log e \cdot \frac{dl}{dt} - \gamma l \log e \cdot \frac{d\beta_R}{dt} \quad (14)$$

$$\frac{dY_{IR}}{dt} = -\gamma \beta_{IR} \log e \cdot \frac{dl}{dt} - \gamma l \log e \cdot \frac{d\beta_{IR}}{dt} \quad (15)$$

FIG. 6A plots the experimentally obtained variations of blood vs. time in a human. FIG. 6B plots the corresponding variation of $\beta_R/\beta_{IR}$ vs. time. The variation of $\beta_R/\beta_{IR}$ vs. time (FIG. 6B) is extremely slow relative to the variation in the quantity of blood ($l$) vs. time (FIG. 6A) for one pulse variation in the quantity of blood. Therefore $d\beta_R/dt$ and $d\beta_{IR}/dt$ can be regarded as zero for one pulse cycle, providing the following equalities:

$$d\beta_R/dt = 0, \, d\beta_{IR}/dt = 0 \quad 16.$$

If the output signals from the differentiation circuits 10 and 10' are fed as inputs to a divising circuit for computation than from equations (15) and (16), the following relationship is true:

$$\frac{dY_R/dt}{dY_{IR}/dt} = \frac{\gamma \beta_R \log e \cdot \frac{dl}{dt}}{\gamma \beta_{IR} \log e \cdot \frac{dl}{dt}} = \frac{\beta_R}{\beta_{IR}} \quad (17)$$

It will be remembered that the oxygen saturation factor S can be calculated when $\beta_R/\beta_{IR}$ is known. By differentiating the $Y_R$ signals from the $Y_{IR}$ signal generating circuits 0 and 0', the fluctuation is the reference level of the Y signals is circumvented, thereby avoiding error in the final indication of oxygen saturation.

The system described to this point is effectively illustrated in FIG. 2 if the division circuit 15 had its respective inputs connected to points $q, q'$, the output of the respective differentiation circuits 10 and 10'. A calculation circuit 16 receives the output of division circuit 15 and uses it to execute either equation (11) or (12). The output of the calculation circuit is supplied to an indicator device 17 which provides an indication of the degree of oxygen saturation in the blood.

To improve the reliability of the indication by indicator 17, supplementary circuits such as amplifiers 11, 11', low-pass filters 12, 12', rectifier circuits 13, 13' and integration circuits 14, 14' are utilized. The filters 12, 12' reduce the noise content of the signals received from the amplifier, 11, 11'. The rectification circuits 13, 13' and integration circuits 14, 14' are used to improve the signal quality of the signals supplied to the division circuit 15.

As an example of specific circuitry that may be utilized to perform the functions of the labeled blocks of FIG. 2, reference may be had to FIGS. 7 – 10. These circuits are presented only as an example, other circuits equivalent in function and seen as well within the purview of a person or ordinary skill in the art. The specific function of the circuitry illustrated is seen as obvious from the figures when taken in combination with the general description of their function. The elements of these circuits, such as operational amplifiers, diodes, capacitors, and switching transistors are well known and understood.

Figure 7:
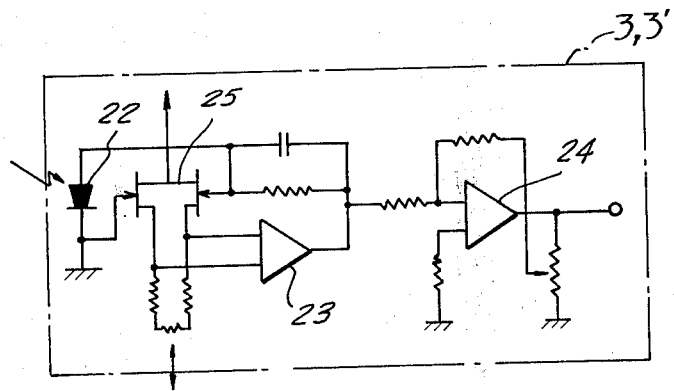
FIG. 7 is a circuit diagram of a photoelectric device that may be used with the present invention.

FIG. 7 is a preferred circuit design of the photoelectric device 3 or 3'. As can be seen from the figure, a photoelectric diode 22 varies the bias on a transistor circuit 25 according to the intensity of light falling on the diode. Amplifiers 23 and 24 provide an output signal voltage $E_{AC+DC}$ that contains both an alternating and steady-state voltage component.

Figure 8:
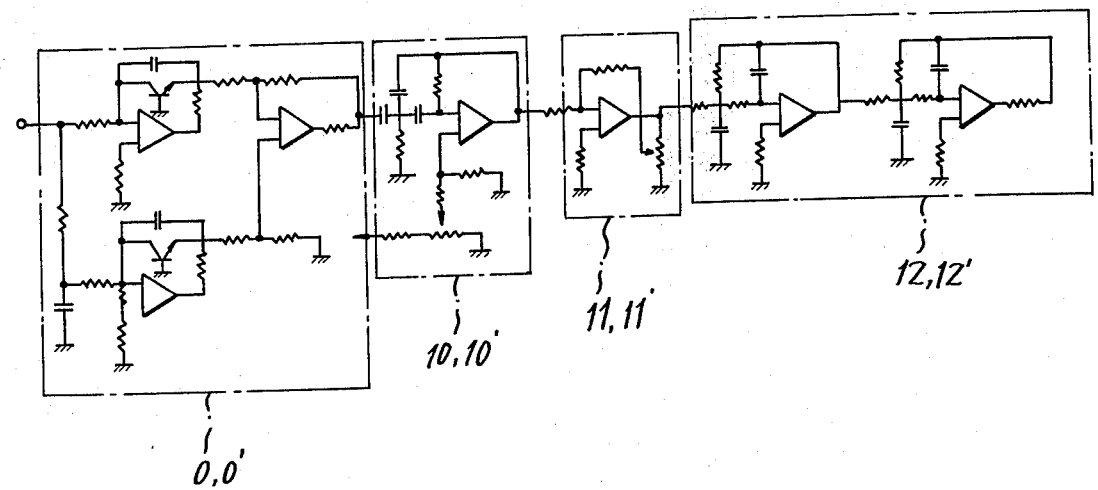
FIG. 8 is a circuit diagram of the various circuits used in the embodiment of FIG. 2.

FIG. 8 is an example of the Y signal generating circuit 0 or 0', the differentiating circuit 10 or 10', the amplifier 11 or 11', and the low-pass filter 12 or 12' of FIG. 2. As can be seen from the illustration straightforward signal processing is utilized.

Figure 9:
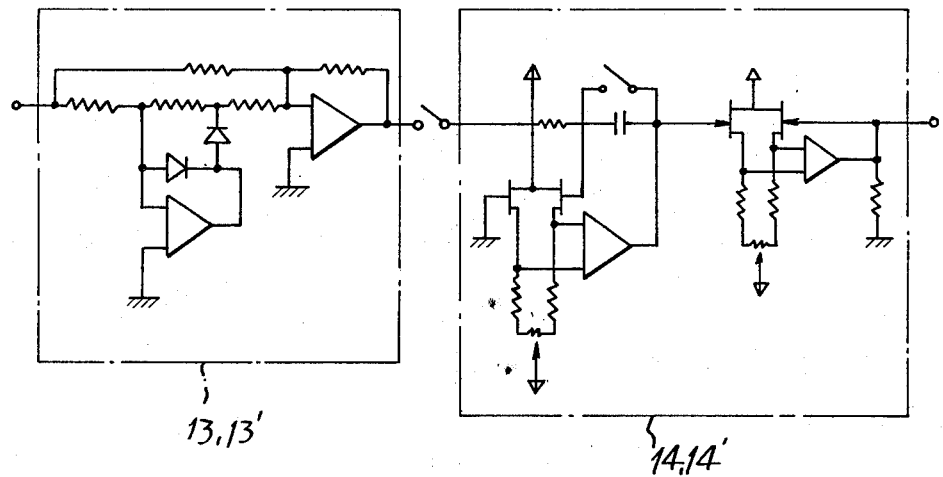
FIG. 9 is a circuit diagram of the rectification and integration circuits of the embodiment of FIG. 2.

FIG. 9 is an example of the rectification circuit 13 or 13', and the integration circuit 14 or 14' of FIG. 2. Here again standard signal processing using diodes, operational amplifiers, etc. is employed.

Figure 10:
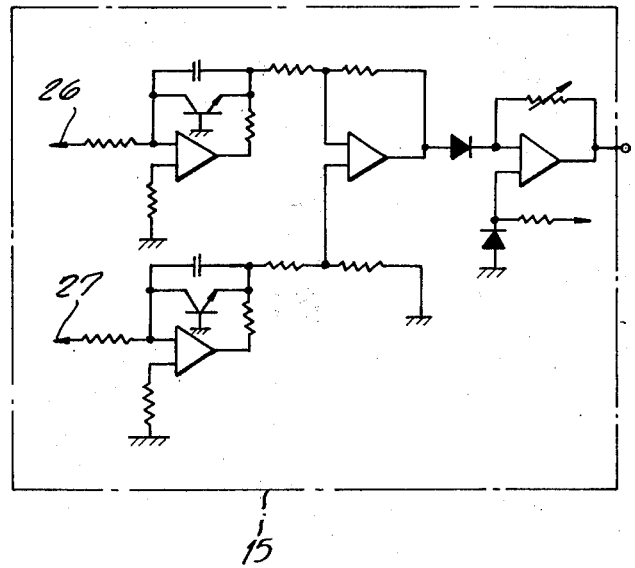
FIG. 10 is a circuit diagram of the division circuit of the embodiment of FIG. 2.

FIG. 10 is an example of a division circuit 15 that may be used as part of the embodiment of FIG. 2. The two input terminals 26, 27 receive signals from integrator circuits 14, 14', respectively.

The calculation circuit 16 of FIG. 2 as was noted, receives the output signals from division circuit 16 and calculates the oxygen saturation (S) in the blood, according to equation (11) or (12). The light absorption coefficient terms of either equation are constants. The operation performed by the calculation circuit amounts to multiplying, dividing, adding, and subtracting utilizing the received variable and the stored constants. The variable is $\beta_R/\beta_{IR}$. If the photoelectric devices 3 and 3' of FIG. 2 are responding to light of 2 different wavelengths when neither is in the infrared region, the calculation circuit must execute equation (11). This amounts to:

1. Multiplying the received variable $\beta_R/\beta_{IR}$ times a constant $A_{IR}(Hb)$ and a constant $A_{IR}(Hb) - A_{IR}(HbO_2)$ to get a first product and second product, respectively.
2. Subtracting a constant $A_R(Hb)$ from the first product to get a difference.
3. Adding a constant $A_R(HbO_2) - A_R(Hb)$ to the second product to get a sum.
4. Dividing the sum into the difference.

If the photoelectric devices 3 and 3' of FIG. 2 are responding to light of 2 different wavelengths when one is in the infrared region, a calculation circuit that executes equation (12) may be utilized. This amounts to:

1. Multiplying the received variable $\beta_R/\beta_{IR}$ by a constant $$\frac{A_{IR}(HbO_2)}{A_R(HbO_2) - A_R(Hb)}$$

to get a product.
2. subtracting a constant $$\frac{A_R(Hb)}{A_R(HbO_2) - A_R(Hb)}$$

from that product. Since $$\frac{dY_R/dt}{dY_{IR}/dt} = \beta_R/\beta_{IR},$$

the calculation circuit 16 takes the variable signal from the division circuit 15 and operates on it, as above noted to obtain oxygen saturation. The exact circuitry for accomplishing the execution of either equation (11) or (12) is seen as well within the purview of a person of ordinary skill in the art. The indicator 17 receives a signal from the calculation circuit 16 that is representative of the amount of oxygen saturation in the arterial blood of a patient being tested. The indicator can either generate a visual or audible indicator of the quantity of oxygen in the arterial blood in any well known manner.

What has been described is a means in an oximeter for obtaining information regarding light absorption by blood in living tissue without compressing the tissue under test and a means for obtaining more reliable and stable readings.

Obviously many modifications and variations of the present invention are possible in light of the above teachings. It is therefore to be understood that within the scope of the appended claims the invention may be practiced otherwise than as specifically described.

What is claimed is:

1. A monitoring device for photoelectrically obtaining information relating to a characteristic of the presence of arterial blood in living tissue comprising:
   a light source capable of providing a light signal;
   means for photoelectrically converting light from the light source, under the optical influence of living tissue, to a first output signal;
   means for separating a direct current component from said first output signal; and
   means for producing an output signal representative of a logarithm of a quotient of said first output signal divided by said separated direct current component.

2. The device of claim 1, wherein said producing means comprises:
   means for dividing said first output signal by said separated direct current component to produce a second output signal; and
   means for converting said second output signal into a logarithm thereof to produce a third output signal whereby said third output signal is representative of a logarithm of a quotient of said first output signal divided by said separated direct current component.

3. An oximeter for obtaining an indication of the degree of oxygen saturation in arterial blood, comprising:
   a light source capable of providing a light signal;
   a pair of means for photoelectrically converting light from said light source, under the optical influence of a living body, to a pair of first output signals, respectively, said pair of photoelectrical converting means being adapted to respond to light signals of different wavelengths;
   a pair of means for respectively computing the corresponding first output signals of said pair of photoelectrical converting means, each of said computing means including:
      means for separating a direct current component from said first output signal;
      means for producing an output signal representative of a logarithm of a quotient of said first output signal divided by said separated direct current component;
   and
   final dividing means for dividing the output signal of one of said producing means by the output signal of the other of said producing means.

4. The oximeter of claim 3, further comprising:
   a first differentiation circuit connected between one of said pair of computing means and said dividing means; and
   a second differentiation circuit connected between the other of said computing means and said dividing means.

5. The oximeter of claim 3, wherein each of said pair of producing means, comprises:

means for dividing said first output signal by said separated direct current component to produce a second output signal; and means for converting said second output signal into a logarithm thereof to produce a third output signal whereby said third output signal is representative of a logarithm of a quotient of said first output signal divided by said separated direct current component.

6. The oximeter of claim 5, further comprising:
a first differentiation circuit connected between one of said pair of computing means and said dividing means; and
a second differentiation circuit connected between the other of said computing means and said dividing means.

7. The oximeter of claim 6, further comprising:
a first low-pass filter, a first rectification circuit connected to said filter and a first integration circuit connected to said rectification circuit, the combination connected between said first differentiation circuit and said final dividing means; and
a second low-pass filter, a second rectification circuit connected to said filter, and a second integration circuit connected to said rectification circuit, the combination connected between said second differentiation circuit and said final dividing means.

8. The oximeter of claim 7, further comprising:
means for calculating the oxygen saturation from the output of said dividing means; and
means for indicating the oxygen saturation calculated by said calculating means.

9. The oximeter of claim 8 wherein said oxygen saturation calculating means, comprises means for executing the equation:

$$S = \frac{A_{IR}(Hb)\beta_R/\beta_{IR} - A_R(Hb)}{(A_{IR}(Hb) - A_{IR}(HbO_2))\beta_R/\beta_{IR} + A_R(HbO_2) - A_R(Hb)}$$

wherein, S is the oxygen saturation of the blood; $\beta_R$ and $\beta_{IR}$ are the light absorption coefficients of the blood in terms of light having a first wavelength (R) and light having a second wavelength (IR), respectively;
$A_R(HbO_2)$ represents the light absorption coefficient of $HbO_2$ in terms of light having a first wavelength;
$A_R(Hb)$ represents the light absorption coefficient of Hb in terms of light having a first wavelength;
$A_{IR}(HbO_2)$ represents the light absorption coefficient of $HbO_2$ in terms of light having a second wavelength, and
$A_{IR}(Hb)$ represents the light absorption coefficient of Hb in terms of light having a second wavelength.

10. The oximeter of claim 8 wherein said oxygen saturation calculating means, comprises means for executing the equation:

$$S = \frac{A_{IR}(HbO_2)}{A_R(HbO_2) - A_R(Hb)} \beta_R/\beta_{IR} - \frac{A_R(Hb)}{A_R(HbO_2) - A_R(Hb)}$$

wherein, S is the oxygen saturation of the blood; $\beta_R$ and $\beta_{IR}$ are the light absorption coefficients of the blood in terms of light having a first wavelength (R) and light having a second wavelength (IR), respectively;
$A_R(HbO_2)$ represents the light absorption coefficient of $HbO_2$ in terms of light having a first wavelength;
$A_R(Hb)$ represents the light absorption coefficient of Hb in terms of light having a first wavelength;
$A_{IR}(HbO_2)$ represents the light absorption coefficient of $HbO_2$ in terms of light having a second wavelength, and
$A_{IR}(Hb)$ represents the light absorption coefficient of Hb in terms of light having a second wavelength.

11. A non-invasive apparatus for obtaining information relating to a characteristic of arterial blood in living tissue comprising:
a source of white light, directed at said living tissue;
means for receiving light transmitted through said living tissue and generating an electrical signal in response thereto;
means for separating a direct current component from said electrical signal; and
means for producing a signal representative of the logarithm of the quotient of the electrical signal divided by the direct current component from said separating means.

12. An oximeter for obtaining an indication of the degree of oxygen saturation in arterial blood, comprising:
a source of light directed at said arterial blood;
first means for responding to light having a first wavelength transmitted through said arterial blood by generating a first signal;
second means for responding to light having a second wavelength transmitted through said arterial blood by generating a second signal;
first means for computing the logarithm of the quotient of the first signal divided by the DC component thereof;
second means for computing the logarithm of the quotient of the second signal divided by the DC component thereof; and
final dividing means for dividing the output of one of said computing means by the output of the other of said computing means.

13. The oximeter of claim 12, wherein said first and second computing means, comprise:
means for separating a DC component from the received signal;
means for dividing the received signal by the DC component; and
means for forming the logarithm of the signal from said dividing means.

14. The oximeter of claim 13, further comprising:
first differentiation means connected between said first computing means and said final dividing means for differentiating the first signal; and
second differentiation means connected between said second computing means and said final dividing means for differentiating the second signal.

15. The oximeter of claim 14, further comprising;
a first low-pass filter, a first rectification circuit connected to said filter and a first integration circuit connected to said rectification circuit, the combination connected between said first differentiation circuit and said final dividing means; and
a second low-pass filter, a second rectification circuit connected to said filter, and a second integration circuit connected to said rectification circuit, the combination connected between said second differentiation circuit and said final dividing means.

16. The oximeter of claim 12, further commprising:

a first differentiation means connected between said first computing means and said final dividing means for differentiating the first signal; and a second differentiation means connected between said second computing means and said final dividing means for differentiating the second signal.

17. The oximeter of claim 16, further comprising:

a first low-pass filter, a first rectification circuit connected to said filter and a first integration circuit connected to said rectification circuit, the combination connected between said first differentiation circuit and said final dividing means; and a second low-pass filter, a second rectification circuit connected to said filter, and a second integration circuit connected to said rectification circuit, the combination connected between said second differentiation circuit and said final dividing means.

18. The oximeter of claim 12, further comprising;

means for calculating the oxygen saturation from the output of said final dividing means by executing the following equation:

$$S = \frac{A_{IR}(Hb)\beta_R/\beta_{IR} - A_R(Hb)}{(A_{IR}(Hb) - A_{IR}(HbO_2))\beta_R/\beta_{IR} + A_R(HbO_2) - A_R(Hb)}$$

wherein, S is the oxygen saturation of the blood;

$\beta_R$ are $\beta_{IR}$ are the light absorption coefficients of the blood in terms of light having a first wavelength (R) and light having a second wavelength (IR), respectively;

$A_R(HbO_2)$ represents the light absorption coefficient of $HbO_2$ in terms of light having a first wavelength;

$A_R(Hb)$ represents the light absorption coefficient of Hb in terms of light having a first wavelength;

$A_{IR}(HbO_2)$ represents the light absorption coefficient of $HbO_2$ in terms of light having a second wavelength, and $A_{IR}(Hb)$ represents the light absorption coefficient of Hb in terms of light having a second wavelength.

19. The oximeter of claim 12, further comprising:

means for calculating the oxygen saturation from the output of said final dividing means by executing the following equation:

$$S = \frac{A_{IR}(HbO_2)}{A_R(HbO_2) - A_R(Hb)} \beta_R/\beta_{IR} - \frac{A_R(Hb)}{A_R(HbO_2) - A_R(Hb)}$$

wherein, S is the oxygen saturation of the blood;

$\beta_R$ and $\beta_{IR}$ are the light absorption coefficients of the blood in terms of light having a first wavelength (R) and light having a second wavelength (IR), respectively;

$A_R(HbO_2)$ represents the light absorption coefficient of $HbO_2$ in terms of light having a first wavelength;

$A_R(Hb)$ represents the light absorption coefficient of Hb in terms of light having a first wavelength;

$A_{IR}(HbO_2)$ represents the light absorption coefficient of $HbO_2$ in terms of light having a second wavelength, and $A_{IR}(Hb)$ represents the light absorption coefficient of Hb in terms of light having a second wavelength.

* * * * *

UNITED STATES PATENT AND TRADEMARK OFFICE
CERTIFICATE OF CORRECTION

PATENT NO. : 3,998,550
DATED : December 21, 1976
INVENTOR(S) : Masaichiro Konishi et al.

It is certified that error appears in the above-identified patent and that said Letters Patent are hereby corrected as shown below:

Col. 3 line 14 after "$(E_{AC+DC})$" insert --of the photoelectric device for the--.

Col. 10, line 68, "commprising" should read -- comprising --.

Signed and Sealed this

Twenty-sixth Day of April 1977

[SEAL]

Attest:

RUTH C. MASON
Attesting Officer

C. MARSHALL DANN
Commissioner of Patents and Trademarks